(12) United States Patent
Hall

(10) Patent No.: US 8,699,025 B2
(45) Date of Patent: Apr. 15, 2014

(54) METHOD AND APPARATUS FOR MEASURING HEXAVALENT CHROMIUM IN WATER

(76) Inventor: Stephen H. Hall, Pasco, WA (US)

( * ) Notice: Subject to any disclaimer, the term of this patent is extended or adjusted under 35 U.S.C. 154(b) by 0 days.

(21) Appl. No.: 13/078,821

(22) Filed: Apr. 1, 2011

(65) Prior Publication Data

US 2011/0242523 A1 Oct. 6, 2011

Related U.S. Application Data

(60) Provisional application No. 61/320,240, filed on Apr. 1, 2010.

(51) Int. Cl.
*G01J 3/46* (2006.01)
(52) U.S. Cl.
USPC ............................ 356/338; 356/51; 356/402
(58) Field of Classification Search
USPC ................. 356/51, 402–425, 432–444, 246; 422/82.05; 250/341.8, 574, 343
See application file for complete search history.

(56) References Cited

U.S. PATENT DOCUMENTS

| | | | | |
|---|---|---|---|---|
| 4,547,070 A | * | 10/1985 | Moll et al. | 356/339 |
| 4,715,710 A | * | 12/1987 | Andersen | 356/246 |
| 4,954,435 A | * | 9/1990 | Krauth | 435/7.93 |
| 4,962,021 A | * | 10/1990 | Meserol et al. | 435/7.92 |
| 5,083,868 A | * | 1/1992 | Anderson | 356/402 |
| 5,872,361 A | * | 2/1999 | Paoli et al. | 250/341.8 |
| 6,445,451 B1 | * | 9/2002 | Douglas-Hamilton et al. | 356/425 |
| 6,844,934 B2 | * | 1/2005 | Retzlaff et al. | 356/436 |
| 7,491,366 B2 | * | 2/2009 | Tokhtuev et al. | 422/82.05 |
| 2003/0058450 A1 | * | 3/2003 | Mosley et al. | 356/436 |
| 2005/0057753 A1 | * | 3/2005 | Mosley et al. | 356/436 |

* cited by examiner

*Primary Examiner* — Sang Nguyen
(74) *Attorney, Agent, or Firm* — Floyd E. Ivey

(57) ABSTRACT

Disclosed and claimed herein is an apparatus and method for measuring hexavalent chromium in water samples using a colorimetric method. The apparatus includes a means for correcting interference due to sample turbidity.

8 Claims, 8 Drawing Sheets

METHOD AND APPARATUS FOR MEASURING HEXAVALENT CHROMIUM IN WATER

APPLICATION PENDING FROM A PROVISIONAL APPLICATION

This application is from U.S. Provisional Application 61/320,240 filed Apr. 1, 2010 and titled "Apparatus and method for measuring hexavalent chromium in water."

FIELD OF THE INVENTION

This invention relates in general to chemical measurements and in particular to the use of colorimetric instruments for measuring the concentration of hexavalent chromium in water.

BACKGROUND OF THE INVENTION

Hexavalent chromium has emerged as a contaminant of significant concern in environmental waters. For example, one source of this contaminant has been the use of hexavalent chromium, in the form of sodium dichromate, to prevent corrosion in the cooling water systems of nuclear reactors. Spills and leaks of sodium dichromate concentrates, and direct discharge of hexavalent chromium-bearing cooling water to the ground surface have released hexavalent chromium to the environment. Some of that hexavalent chromium has reached groundwater aquifers.

For the purposes of environmental monitoring of hexavalent chromium in wells and water bodies, and for controlling engineered processes used to remediate contaminated water, frequent measurements of hexavalent chromium are required. Visible range colorimetry based on the Beer-Lambert law is the most commonly used analytical method used to perform the measurements. However, the visible range colorimetric method depends on treating samples with chemical reagents to react with the hexavalent chromium to produce a visible red-violet color whose intensity is related to the concentration of the hexavalent chromium in the sample.

While sensitive and accurate, the visible range colorimetric method has disadvantages. The samples often require filtration to eliminate turbidity, caused by suspended particulate matter, which interferes with colorimetric measurements. Because of the need for both filtration and chemical treatment, the method is not readily adaptable to continuous process monitoring or to in situ measurements in wells or water bodies. Further, the chemically-treated water samples, along with ancillary packaging materials, single-use reagent ampoules, and the like, constitute waste that in itself requires careful and appropriate handling and disposal.

The patents and publications referred to herein are provided herewith in an Information Disclosure Statement in accordance with 37 CFR 1.97.

SUMMARY OF THE INVENTION

The present invention comprises a modified colorimeter and analytical method, the application of which avoids the aforementioned disadvantages in two ways. First, the wavelength of the modified colorimeter's incident beam is in the near ultraviolet, and preferably within the range from approximately 365 nm to 375 nm for maximum analytical sensitivity. Within this range, the peak absorptivity of hexavalent chromium, as the chromate ion, is comparable to the absorptivity of the colored compound developed in the visible range colorimetric method. No chemical treatment of the water sample is required because at the neutral or near-neutral pH of environmental water samples, chromate is by far the predominant form of hexavalent chromium, and the strong absorbance of ultraviolet light in the specified wavelength range is an inherent attribute of the chromate ion. Thus, the analytical sensitivity of the invention is comparable to that of the visible range colorimetric method, but with no need for chemical treatment of the sample.

Second, the modified colorimeter uses two light sensors. One sensor is used to measure the intensity of the transmitted ultraviolet beam per the usual practice of colorimetry. A second sensor is positioned approximately ninety degrees from the axis of the transmitted ultraviolet beam to measure light scattered from the beam by suspended particulates (i.e., a nephelometric measurement of turbidity). By measuring both the transmitted light and the scattered light, the analytical measurement can be corrected for the interference caused by turbidity. Thus, the need to filter the sample is omitted.

By eliminating the need for chemical treatment and filtration of water samples, practical instruments can be deployed to directly measure hexavalent chromium concentration.

BRIEF DESCRIPTION OF THE FIGURES

The foregoing and other features and advantages of the present invention will become more readily appreciated as the same become better understood by reference to the following detailed description of the preferred embodiment of the invention when taken in conjunction with the accompanying drawings, wherein.

DETAILED DESCRIPTION OF THE INVENTION

Figure 1:
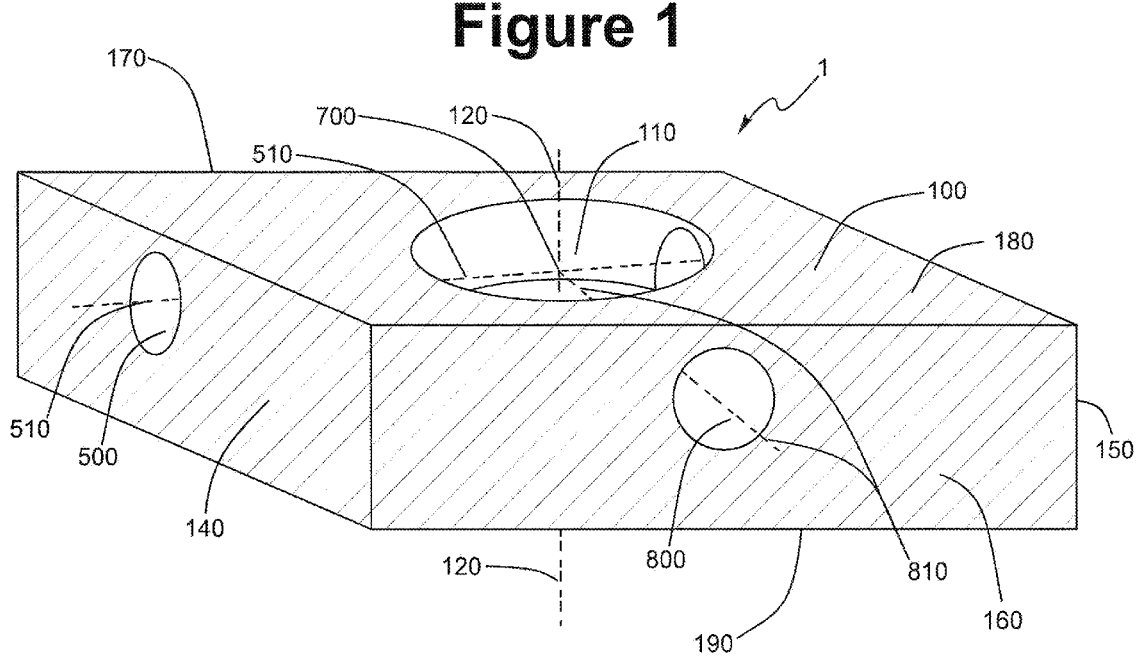
FIGS. 1 and 2 depict a colorimeter (1) with a colorimeter body (100), sample chamber (110), sample chamber axis (120), a first side (140), a second side (150), a front (160), a back (170), a top (180) and a bottom (190). Also shown are a first light tunnel bore (500), an axis of first light tunnel bore (510), a
second light tunnel bore (800), an axis of second light tunnel bore (810) and a point of intersection (700). Seen in FIG. 2 is a sample vessel (200). Also seen in FIG. 2 is section 3 forming the sectional plane (3) of the device.
Figure 2:
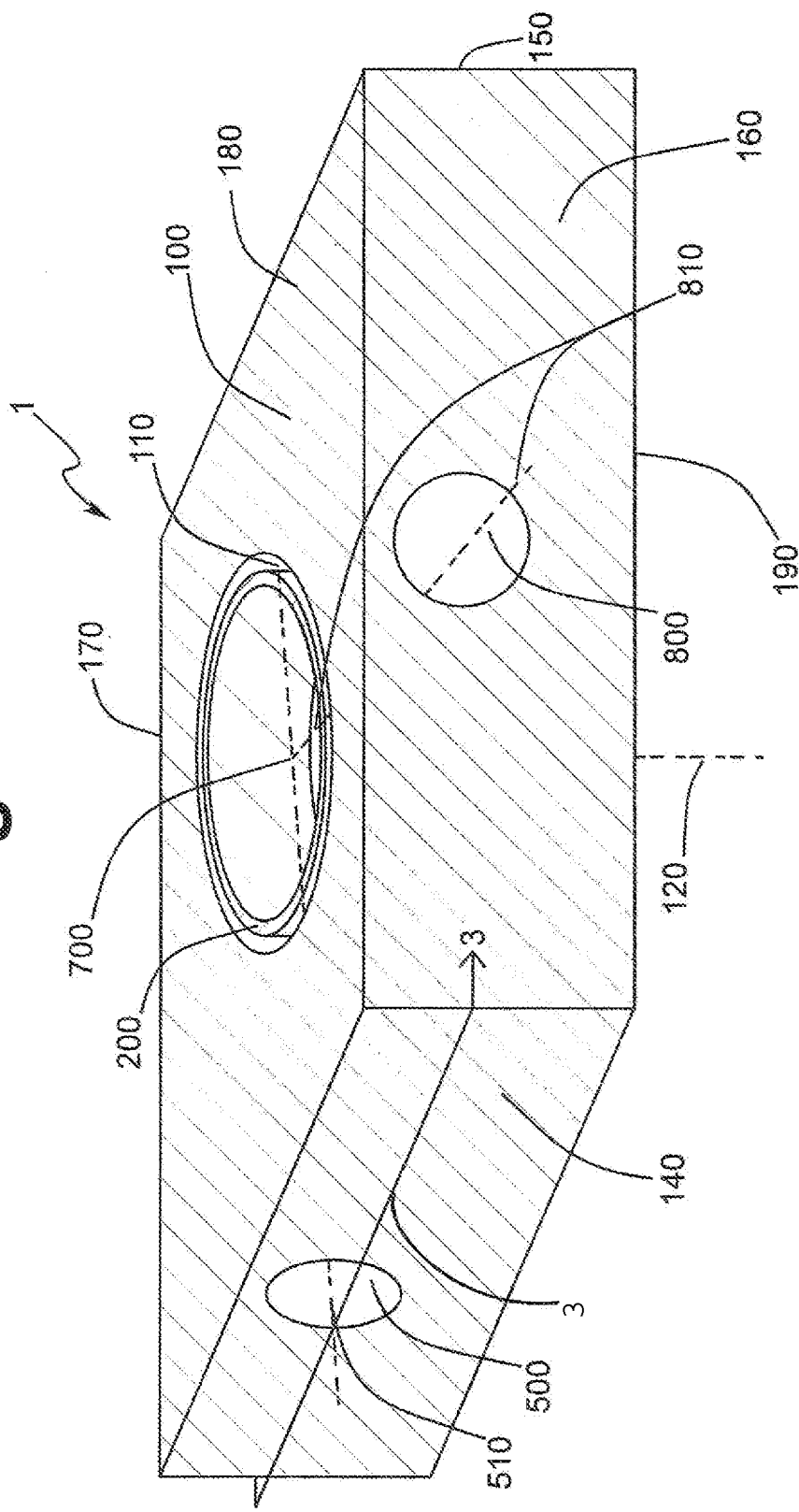

The preferred embodiment of the apparatus of this disclosure is seen in FIG. 1 through FIG. 4 illustrating colorimeter (1) showing a colorimeter body (100) having a sample chamber (110), first side (140), a second side (150), a front (160), a back (170), a top (180) and a bottom (190). The sample chamber (110) is generally a cylinder, closed at the bottom (190) and open at the top (180) shaped having an upwardly directed sample chamber axis (120) which is generally orthogonal to the bottom (190) and centrally positioned within the sample chamber (110). A person of ordinary skill in sample and measurement arts will recognize that the shape and size of the sample chamber (110) accommodates the size and shape of sample vessels (200) purposed for the particular testing to be accomplished. Such sample vessels (200) may generally be cylindrical in shape. In the preferred embodiment the sample vessel (200) is transparent.

FIG. 1 through 4 also illustrate a first light tunnel bore (500) extending from the first side (140) through the second side (150) having an axis of first light tunnel bore (510) generally centrally positioned within the first light tunnel bore (500) and intersects and is generally orthogonal to the sample chamber axis (120). A second light tunnel bore (800), having an axis of second light tunnel bore (810) generally centrally positioned within the second light tunnel bore (800), extends from the front (160) and into the sample chamber (110). The axis of second light tunnel bore (810) transits the second light tunnel bore (800), the sample vessel (200) and the contents of the sample vessel (200) and is intersects the sample chamber axis (120). The contents of the sample vessel (200) is primarily water, for the purpose of measurement of hexavalent chromium in water, and the sample vessel (200) is generally glass. The second light tunnel bore (800) is generally filled with air. The scattered light path (130) at scattered light path angle α (135) is refracted upon leaving the sample vessel (200) and entering air. The light tunnel bore angle Ω (900) is generally equal to the angle of the path through air of the refracted light exiting the sample vessel (200), and the axis of the second light tunnel bore (810) is generally coincident with the path through air of the refracted light. The axis of the second light tunnel bore (810) intersects the sample chamber axis (120) at the point of intersection (700) only when light tunnel bore angle Ω (900) and scattered light path angle α (135) are equal to 0°. When second light tunnel bore angle Ω (900) is 30° and the radius of the sample vessel (200) is 12.5 mm, the scattered light path angle alpha is approximately 22° and the axis of second light tunnel bore (810) intersects the sample chamber axis (120) at a point shifted approximately 2 mm from the point of intersection (700). Those of ordinary skills in these measurement arts will recognize that samples other than primarily water will have different refraction characteristics.

The dimensions and angular relationships of the colorimeter body (100), the first tunnel bore (500), the axis of first tunnel bore (510), the second tunnel bore (800), the axis of second tunnel bore (810), sample chamber (110), the sample chamber axis (120) and the sample vessel (200) are such that the axis of first light tunnel bore (510), sample chamber axis (120) and scattered light path (130) are co-incident at a point of intersection (700). In the preferred embodiment the axis of second light tunnel bore (810) intersects the sample chamber axis (120) at an angle of between 45° and 90°.

A light source (300) shines a beam of nearly-monochromatic ultraviolet light through a sample vessel (200) to a photodetector (400) via a first light tunnel bore (500). The light source (300) light or beam or incident beam is co-incident with a centrally positioned first light tunnel bore axis (510). The first light tunnel bore (500) also serves to collimate the light beam. The method of having light from the light source (300) passing through a sample vessel (200) to a first light detector (400) will be immediately familiar to the practitioner of colorimetry, and it is understood that the colorimeter (1) and colorimeter shown in FIG. 1 through FIG. 4 must be shielded, such as with a light tight box, from external light sources during operation. That is, the body (100), circuit board from FIG. 5 and other components will normally be contained within a light tight box.

To correct for the effect of turbidity, the present invention uses a second photodetector (600) which measures the fraction of the incident light beam that is scattered by the suspended particulate matter in the sample vessel (200) and which reaches second photodetector (600) via the second light tunnel bore (800). The relationship of the light transmitted via the second light tunnel (800) to the second photodetector (600) will be immediately familiar to the practitioner of nephelometry. The axis of second light tunnel bore (810) extends to the second photodetector (600) from a point on the sample chamber axis (120) at or near the point of intersection (700) which lies along the light path from the light source (300) to the first photodetector (400) and is at the approximate mid-point of the sample vessel. In FIG. 1, the axis of first light tunnel bore (510) is seen to lie within the sectional plane of the figure. However, while the axis of second light tunnel bore (810) is preferably, but not necessarily, normal to the axis of first light tunnel bore (510) it is not required to lie within the sectional plane of FIG. 1.

Figure 3:
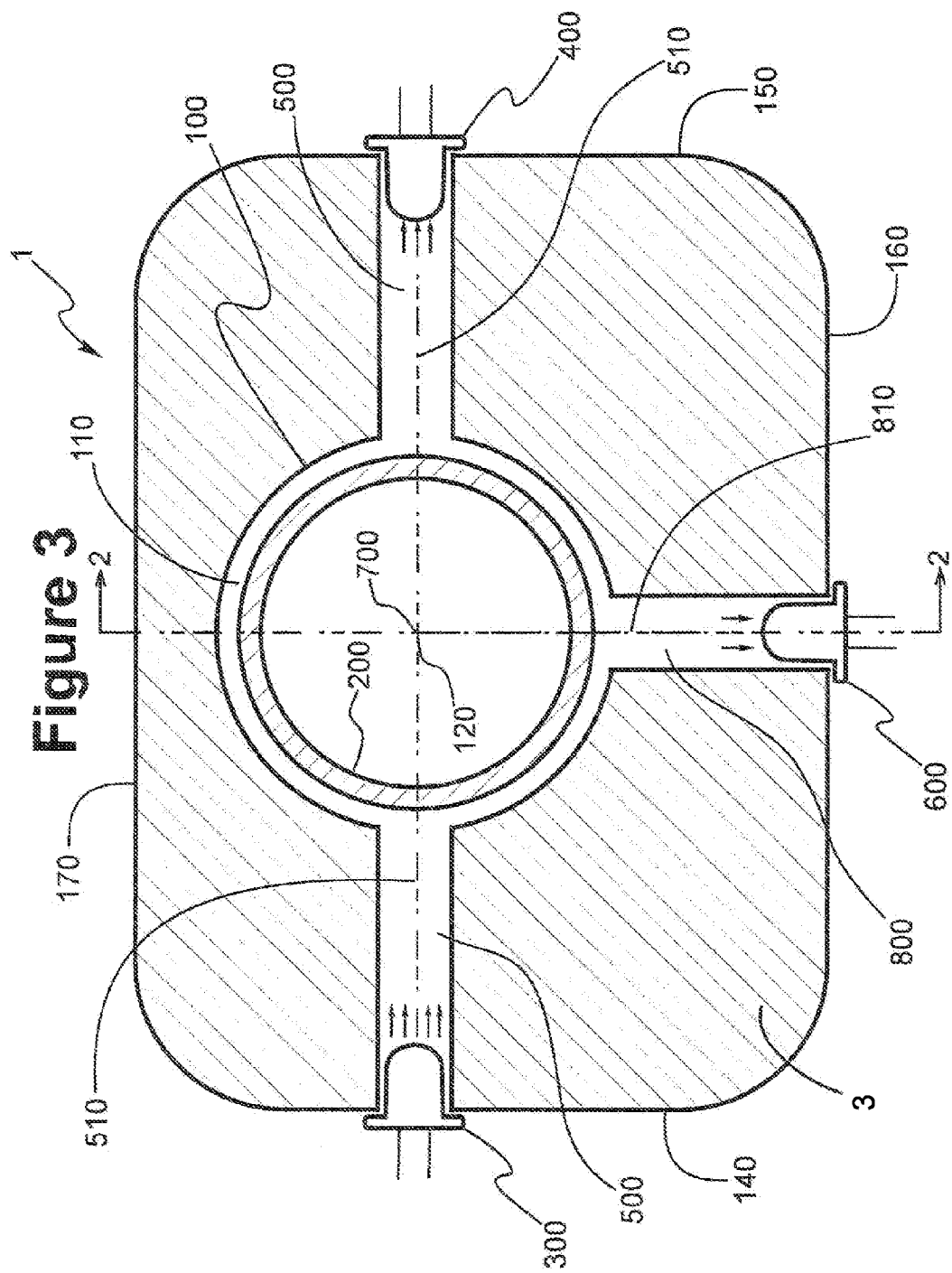
FIG. 3 is a section from FIG. 2 illustrating structure shown in FIG. 1 and FIG. 2 and additionally showing a light source (300), a first photodetector (400) and a second photodetector (600) and the sectional plane (3) of the device.
Figure 4:
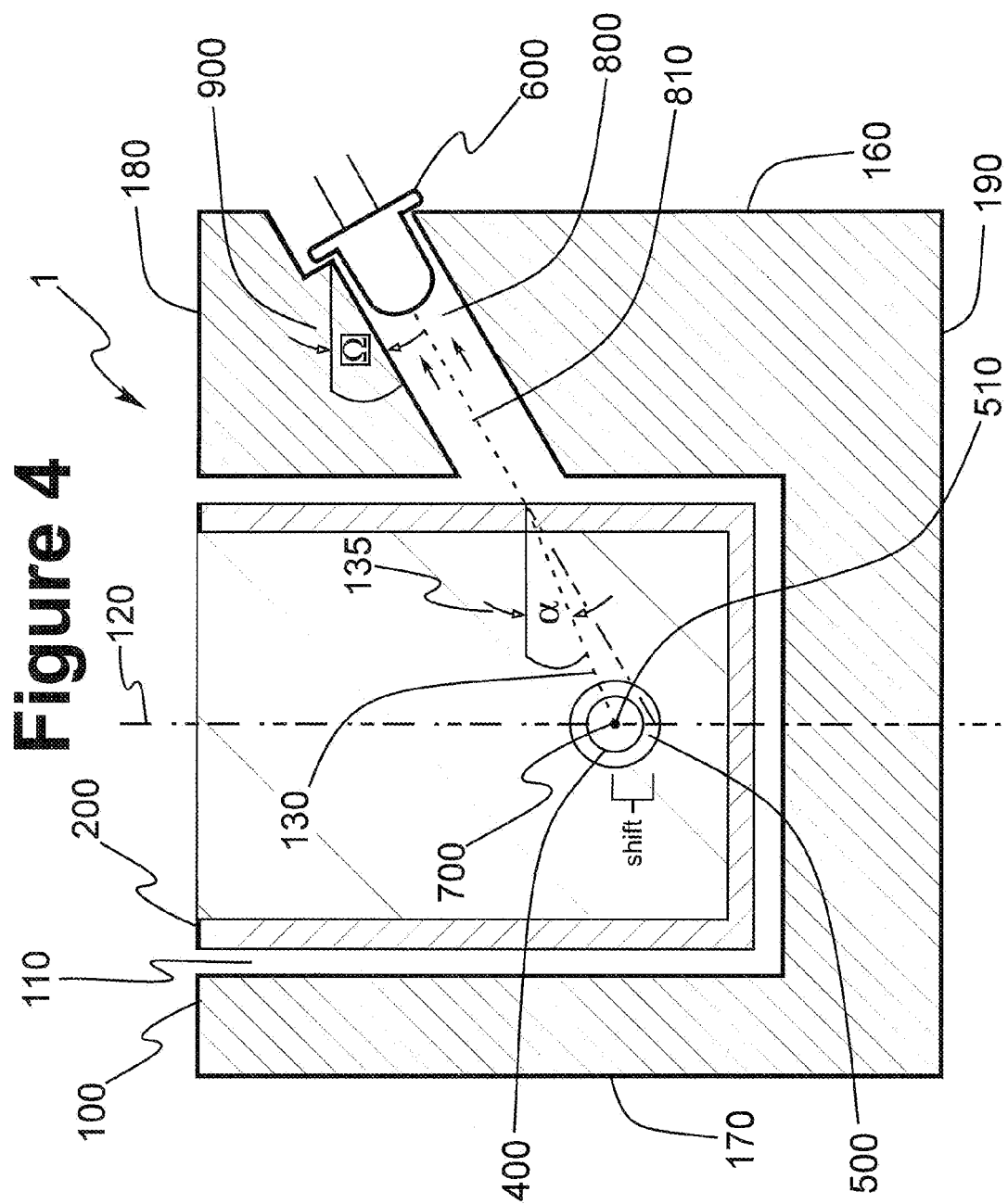
FIG. 4 illustrates a section view from FIG. 3 showing a colorimeter (1), a colorimeter body (100), a sample chamber (110), a sample chamber axis (120), a scattered light path (130) and a scattered light path angle (135). Also seen is a front (160), a back (170), a top (180) and a bottom (190). Also illustrated is a sample vessel (200), and a light tunnel bore angle Ω (900).

FIG. 4 is a cross-sectional view from FIG. 3 and normal to the axis of first light tunnel bore (500) of FIG. 1, and which represents the plane that includes the axis of the second light tunnel bore (810) of FIG. 1. In FIG. 4, the axis of second light tunnel bore (810) has been raised 30° from the sample chamber axis (120), but is positioned to intercept light from point of intersection (700) of FIG. 1 through 4. The purpose of positioning the second light tunnel bore (800) at an angle as shown in FIG. 4 is to minimize reflection of stray light from the walls of sample chamber (110) or sample vessel (200) to the second photodetector (600). Note that in FIG. 4, the axis of second light tunnel bore (810) has been shifted downward by approximately 2 mm to account for the index of refraction of water. The amount of shift is specific to the angle (30°) and to the dimensions of the colorimeter (1) described herein relative to the preferred embodiment for the measurement of hexavalent chromium in water.

The interior surfaces of the colorimeter sample chamber (110), but not of transparent sample vessel (200), should be non-reflective. The configuration of the first light tunnel bore (500) and second light tunnel bore (800) of the colorimeter (1) are the preferred embodiment representing a simple means to shield the second photodetector (600) from the light from the light source (300).

Figure 7:
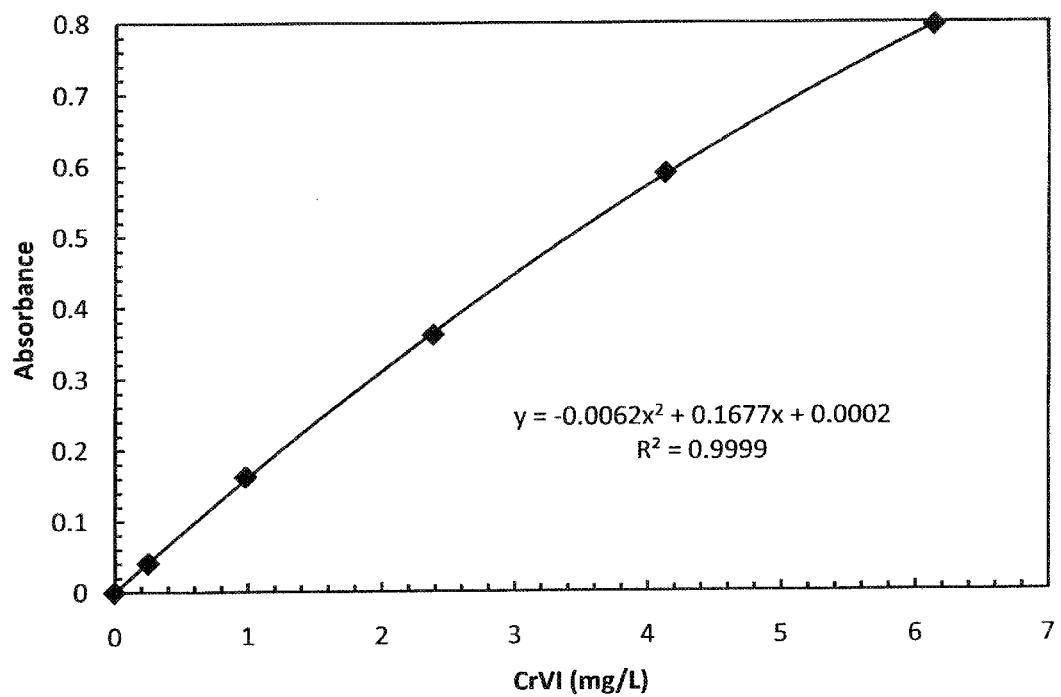
FIGS. 7 and 8 show graphed calibration data where optical absorbance is a function of hexavalent chromium concentration.
Figure 8:
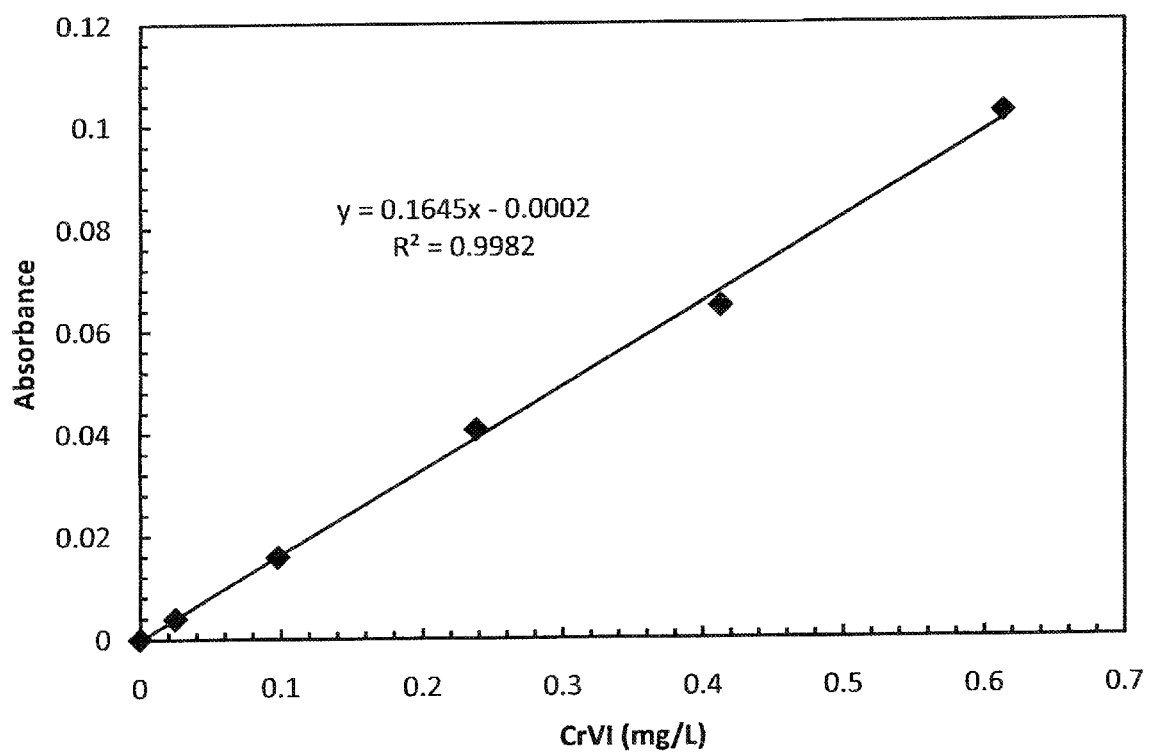

FIGS. 7 and 8 represent the results of calibrating the invention using solutions containing known concentrations of chromate ion, as hexavalent chromium ($Cr^{+6}$) within the ranges 0 to 7 mg/L and 0 to 0.7 mg/L, respectively.

Technical specifications of the prototype used to generate the performance data and its individual components are discussed as follows, and represent a preferred embodiment of the invention, with the second light tunnel bore (800) elevated 30° as shown in FIG. 4. In the preferred embodiment the first light tunnel bore (500) and the second light tunnel bore (800) are bored 5 mm in diameter. The second light tunnel (800) is approximately 38 mm long. The first light tunnel bore (500) from the first side (140) to the point of intersection (700) and from the second side (150) to the point of intersection (700) are each approximately 33 mm long. The sample chamber (110) is approximately 28 mm in diameter, and the outer and inner diameters of the sample vessel are approximately 27 mm and 25 mm, respectively.

Figure 5:
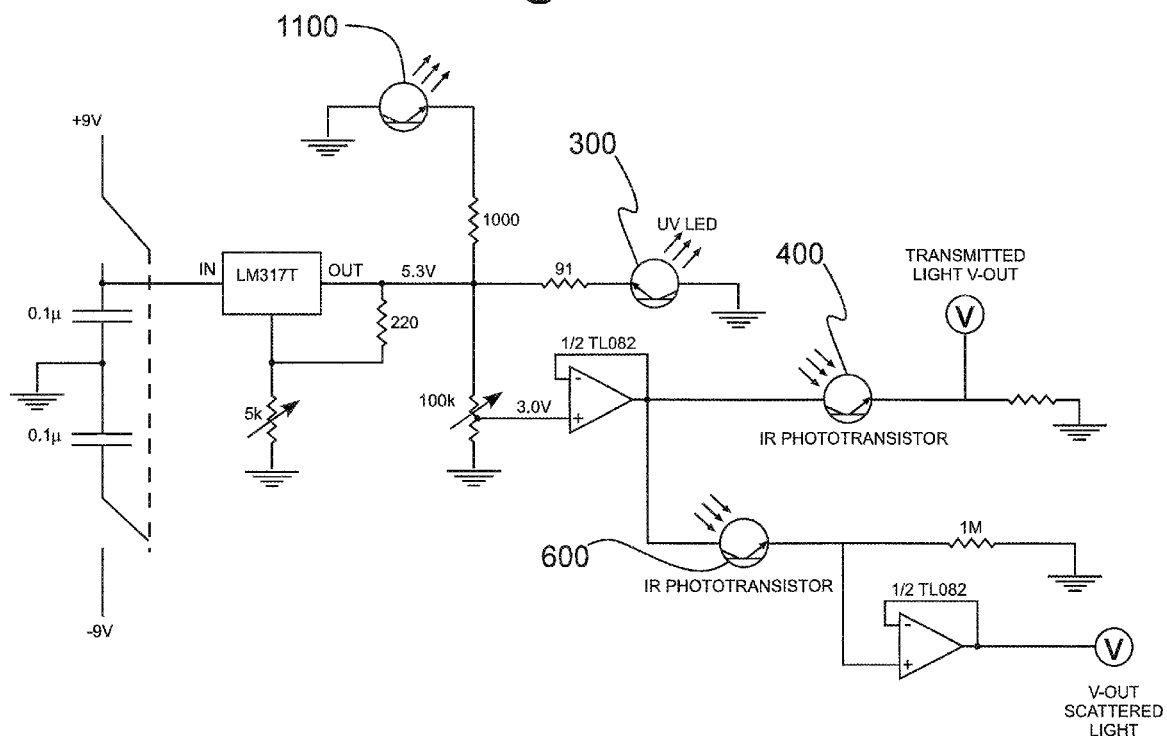
FIG. 5 shows the electronic circuit of the colorimeter (1) additionally indicating a light source (300), a first photodetector (400), a second photodetector (600) and a power indicator LED (1100).

The peak wavelength of the NICHIA® #NSPU510CS light-emitting diode used as the light source (300) and to produce the an incident beam was 375 nm according to the manufacturer's specifications, and it was operated at 18 mA for testing. The first photodetector (400) and the second photodetector (600), used for measuring the intensity of both the transmitted and scattered light, were RADIO SHACK® infrared phototransistors, part #RS 276-145A, biased at 3 volts for use as photoconductive sensors. FIG. 5 is the complete electronic circuit used in the prototype instrument. A stabilized voltage of 5.3 V was provided by the LM317T adjustable voltage regulator, RADIO SHACK® part #RS 276-1778. A TL082 dual JFET input operational amplifier (RADIO SHACK® part #RS 276-1715) was used in the circuit with both inputs used as voltage followers as shown in FIG. 5. A red LED (1100) is used to indicate that power is switched on.

Digital voltmeters with input resistance of at least 10 megaohms were used to measure the output signals. The intensity of light from the incident beam that reaches the first photodetector (400) is attenuated by absorption as well as by the light scattering caused by suspended particulate matter, and both absorption and scattering contribute to the measured apparent absorbance. In contrast, the intensity of light scattered towards the second photodetector (600) increases with increased turbidity, but is decreased by absorption. It is this relationship between light absorption and light scattering in the optical paths of the colorimeter (1) that is basis of the method for correcting measurements for turbidity.

Figure 6:
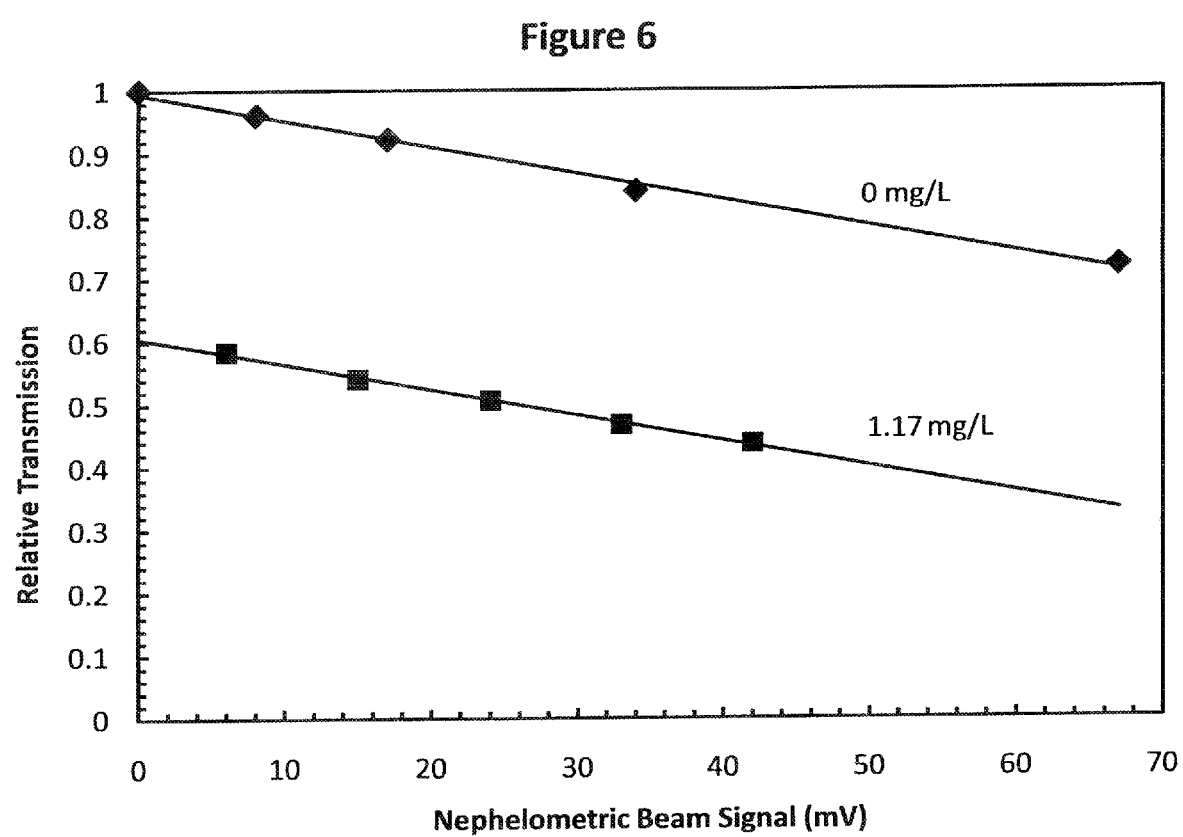
FIG. 6 shows graphs of relative light transmission versus an electronic signal representing scattered light intensity for two concentration levels of hexavalent chromium.

FIG. 6 includes two graphed plots where percent transmittance, determined from the electronic signal measured at the first photodetector (400), is shown plotted against the scattered light signal measured at the second photodetector (600). Each plot represents a series of measurements made on samples that have a constant hexavalent chromium concentration but with progressively increased turbidity. The upper plot has a chromium concentration of 0 mg/L, and the lower plot has a concentration of 1.17 mg/L. Inspection of the FIG. 6 shows that the two sets of plotted data are linear and parallel within the ranges shown. The mean slope of the plots of FIG. 6 multiplied by the signal from second photodetector (600) yields a correction to be added to the signal from the first photodetector (400).

While various embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims. Various features of the invention are set forth in the appended claims.

I claim:

1. An apparatus for measuring the amount of a chemical within a turbid sample comprising:
    a colorimeter (1) having a colorimeter body (100), the body (100) having a sample chamber (110); a sample vessel (200) is accommodated by the sample chamber (110) and is placed within the sample chamber (110); a sample is placed within the sample vessel (200); and,
        a light source (300) is affixed to the body (100) and light, an incident beam, from the light source (300) is directed toward and illuminates the sample vessel (200); a first photodetector (400), affixed to the body (100), is aligned with the light source (300) and the incident beam passing through the sample vessel (200) and is illuminated by light passing through the sample vessel (200); the first photodetector (400) is distal to the light source (300) and sample vessel (200); and,
    a second photodetector (600) is generally orthogonal to the incident beam from the light source (300); the second photodetector (600) is aligned with the sample vessel (110) and is illuminated by light scattered from the incident beam from the light source (300) as said incident beam passes through the sample vessel (200); and,
    the intensity of light from the incident beam that reaches the first photodetector (400) is attenuated by absorption as well as by the light scattering caused by suspended particulate matter within the sample vessel (200), and both absorption and scattering contribute to the measured apparent absorbance; and,
    the intensity of light scattered towards the second photodetector (600) increases with increased turbidity, but is decreased by absorption; and,
    the relationship between light absorption and light scattering in the optical paths of the colorimeter (1) is the basis of the method for correcting measurements for turbidity.

2. The apparatus of claim 1 further comprising:
    the body has a first side (140), a second side (150), a front (160), a back (170), a top (180) and a bottom (190); and,
    the sample chamber (110) is generally a cylinder, closed at the bottom (190) and open at the top (180) having an upwardly directed sample chamber axis (120) which is generally orthogonal to the bottom (190) and centrally positioned within the sample chamber (110); and the sample vessel (200) is generally cylindrical in shape and transparent; and
    a first light tunnel bore (500) extends from the first side (140) through the second side (150) having an axis of first light tunnel bore (510); the axis of first light tunnel bore (510) is generally centrally positioned within the first light tunnel bore (500) and intersects and is orthogonal to the sample chamber axis (120); and
    a second light tunnel bore (800), having an axis of second light tunnel bore (810) generally centrally positioned within the second light tunnel bore (800), extends from the front (160) and into the sample chamber (110); and the axis of second light tunnel bore (810) transits the second light tunnel bore (800), the sample vessel (200) and the contents of the sample vessel (200) and intersects the sample chamber axis (120).

3. The apparatus of claim 2 further comprising:
    the dimensions and angular relationships of the colorimeter body (100), the first tunnel bore (500), the axis of first tunnel bore (510), the second tunnel bore (800), the axis of second tunnel bore (810), sample chamber (110), the sample chamber axis (120) and the sample vessel (200) are such that the axis of first light tunnel bore (510), sample chamber axis (135) and refraction axis (130) are co-incident at a point of intersection (700).

4. The apparatus of claim 3 further comprising:
    the axis of second light tunnel bore (810) intersects the sample chamber axis (120) at an angle of between 50° and 80° from the vertical; and the axis of second light tunnel bore (810) is at an angle to the sample chamber axis (130) of 60°; and
    the light source (300) shines a beam of nearly-monochromatic ultraviolet light through the sample vessel (200) to a the first photodetector (400) via the first light tunnel bore (500) co-incident with the centrally positioned first light tunnel bore axis (510); and, the colorimeter (1) is shielded from external light sources during operation; and, correction for the effect of turbidity is by the use of a second photodetector (600) which measures the fraction of the incident light beam that is scattered by the suspended particulate matter in the sample vessel (200) and which reaches second photodetector (600) via the second light tunnel bore (800).

5. An apparatus for measuring the amount of a chemical within a turbid sample comprising:

a colorimeter (1) having a colorimeter body (100) and having a sample chamber (110), a first side (140), a second side (150), a front (160), a back (170), a top (180) and a bottom (190); and the sample chamber (110) is generally a cylinder, closed at the bottom (190) and open at the top (180) having an upwardly directed sample chamber axis (120) which is generally orthogonal to the bottom (190) and centrally positioned within the sample chamber (110); and the shape and size of the sample chamber (110) accommodates the size and shape of sample vessels (200) purposed for the particular testing to be accomplished where the sample vessels (200) may generally be cylindrical in shape and transparent; and a first light tunnel bore (500) extends from the first side (140) through the second side (150) having an axis of first light tunnel bore (510) generally centrally positioned within the first light tunnel bore (500) and with and intersects and is orthogonal to the sample chamber axis (120); and a second light tunnel bore (800), having an axis of second light tunnel bore (810) generally centrally positioned within the second light tunnel bore (800), extends from the front (160) and into the sample chamber (110); and the axis of second light tunnel bore (810) transits the second light tunnel bore (800), the sample vessel (200) and the contents of the sample vessel (200) and is intersects the sample chamber axis (120); and the sample vessel (200) is generally glass resulting in a scattered light path (130) intersects the sample chamber axis (120) and intersects the axis of second light tunnel bore (810) upon leaving the sample vessel (200) and entering air; and, the dimensions and angular relationships of the colorimeter body (100), the first tunnel bore (500), the axis of first tunnel bore (510), the second tunnel bore (800), the axis of second tunnel bore (810), sample chamber (110), the sample chamber axis (120) and the sample vessel (200) are such that the axis of first light tunnel bore (510), sample chamber axis (120) and scattered light path (130) are co-incident at a point of intersection (700); and, the axis of second light tunnel bore (810) intersects the sample chamber axis (120) at an angle of between 45° and 90° from the vertical; and, the light source (300) shines a beam of nearly-monochromatic ultraviolet light through the sample vessel (200) to a the first photodetector (400) via the first light tunnel bore (500) co-incident with the centrally positioned first light tunnel bore axis (510); and, where the colorimeter (1) is shielded from external light sources during operation; and, correction for the effect of turbidity is by the use of a second photodetector (600) which measures the fraction of the incident light beam that is scattered by the suspended particulate matter in the sample vessel (200) and which reaches second photodetector (600) via the second light tunnel bore (800); and, the axis of second light tunnel bore (810) extends to the second photodetector (600) from a point on the sample chamber axis (120) at or near the point of intersection (700) which lies along the light path from the light source (300) to the first photodetector (400) and is at the approximate mid-point of the sample vessel; and, the axis of first light tunnel bore (510) lies within the sectional plane (3) the while the axis of second light tunnel bore (810) is preferably, but not necessarily, normal to the axis of first light tunnel bore (510) and is not required to lie within the sectional plane (3); and, the axis of second light tunnel bore (810) is at an angle of from 45° to 90° from the sample chamber axis (120), but is positioned to intercept light originating from point of intersection (700); the positioning of the second light tunnel bore (800) at an angle minimizes reflection of stray light from the walls of sample chamber (110) or the sample vessel (200) to the second photodetector (600); and, the axis of second light tunnel bore (810) has been shifted downward by approximately 2 mm to account for the index of refraction of water; the amount of shift is specific to a light tunnel bore angle 12 (900) of 30°; a cylindrical sample vessel (200) having a 25 to 27 ram diameter and to the dimensions of the colorimeter (1) described herein relative to the preferred embodiment for the measurement of hexavalent chromium in water; and, the interior surfaces of the colorimeter sample chamber (110), but not of transparent sample vessel (200), should be non-reflective; the configuration of the first light tunnel bore (500) and second light tunnel bore (800) of the colorimeter (1) are the preferred embodiment representing a simple means to shield the second photodetector (800) from the light from the light source (300); and, the first light tunnel bore (500) and the second light tunnel bore (800) are bored 5 mm in diameter; the second light tunnel (800) is approximately 38 mm long; the first light tunnel bore (500) from the first side (140) to the point of intersection (700) and from the second side (150) to the point of intersection (700) are each approximately 33 mm long; the sample chamber (110) is approximately 28 mm in diameter, and the outer and inner diameters of the sample vessel are approximately 27 mm and 25 ram, respectively; and, the incident beam of the light source (300) is in the range of 367 to 375 nm; the slight source (300) is provided by a light-emitting diode, the first photodetector (400) and the second photodetector (800), used for measuring the intensity of both the transmitted and scattered light, are infrared phototransistors used as photoconductive sensors; and, stabilized voltage is provided by an adjustable voltage regulator, an operational amplifier is used with inputs used as voltage followers; and, a red LED (1100) is used to indicate that power is switched on.

6. An Apparatus for Measuring the amount of a chemical within a turbid sample comprising:

a colorimeter (1) having a colorimeter body (100), the body (100) having a sample chamber (110); a sample vessel (200) is accommodated by the sample chamber (110) and is placed within the sample chamber (110); a sample is placed within the sample vessel (200); and, a light source (300) is affixed to the body (100) and light, an incident beam, from the light source (300) is directed toward and illuminates the sample vessel (200); a first photodetector (400), affixed to the body (100), is aligned with the light source (300) and the incident beam passing through the sample vessel (200) and is illuminated by light passing through the sample vessel (200); the first photodetector (400) is distal to the light source (300) and sample vessel (200); and, a second photodetector (600) is generally orthogonal to the incident beam from the light source (300); the second photodetector (600) is aligned with the sample vessel (110) and is illuminated by light scattered from the incident beam from the light source (300) as said incident beam passes through the sample vessel (200); and, the intensity of light from the incident beam that reaches the first photodetector (400) is attenuated by absorption as well as by the light scattering caused by suspended particulate matter within the sample vessel (200), and both absorption and scattering contribute to the measured apparent absorbance; and, the intensity of light scattered towards the second photodetector (600) increases with increased turbidity, but is decreased by absorption; and, the relationship between light absorption and light scattering in the optical paths of the colorimeter (1) is the basis of the method for correcting measurements for turbidity; and, the body has a first side (140), a second side (150), a front (160), a back (170), a top (180) and a bottom (190); and, the sample chamber (110) is generally a cylinder, closed at the bottom (190) and open at the top (180) having an upwardly directed sample chamber axis (120) which is generally orthogonal to the bottom (190) and centrally positioned within the sample chamber (110); and the sample vessel (200) is generally cylindrical in shape and transparent; and a first light tunnel bore (500) extends from the first side (140) through the second side (150) having an axis of first light tunnel bore (510); the axis of first light tunnel bore (510) is generally centrally positioned within the first light tunnel bore (500) and intersects and is orthogonal to the sample chamber axis (120); and a second light tunnel bore (800), having an axis of second light tunnel bore (810) generally centrally positioned within the second light tunnel bore (800), extends from the front (160) and into the sample chamber (110); and the axis of second light tunnel bore (810) transits the second light tunnel bore (800), the sample vessel (200) and the contents of the sample vessel (200) and intersects the sample chamber axis (120); and the dimensions and angular relationships of the colorimeter body (100), the first tunnel bore (500), the axis of first tunnel bore (510), the second tunnel bore (800), the axis of second tunnel bore (810), sample chamber (110), the sample chamber axis (120) and the sample vessel (200) are such that the axis of first light tunnel bore (510), sample chamber axis (135) and refraction axis (130) are co-incident at a point of intersection (700); and the axis of second light tunnel bore (810) intersects the sample chamber axis (120) at an angle of between 50° and 80° from the vertical; and the axis of second light tunnel bore (810) is at an angle to the sample chamber axis (130) of 60°; and the light source (300) shines a beam of nearly-monochromatic ultraviolet light through the sample vessel (200) to a the first photodetector (400) via the first light tunnel bore (500) co-incident with the centrally positioned first light tunnel bore axis (510); and, the colorimeter (1) is shielded from external light sources during operation; and, correction for the effect of turbidity is by the use of a second photodetector (600) which measures the fraction of the incident light beam that is scattered by the suspended particulate matter in the sample vessel (200) and which reaches second photodetector (600) via the second light tunnel bore (800).

7. The apparatus of claim 6 further comprising: the axis of second light tunnel bore (810) extends to the second photodetector (600) from the point of intersection (700) which lies along the light path from the light source (300) to the first photodetector (400) and is at the approximate mid-point of the sample vessel; and, the axis of first light tunnel bore (810) lies within the sectional plane (3) of the figure while the axis of second light tunnel bore (810) is preferably, but not necessarily, normal to the axis of first light tunnel bore (510) and is not required to lie within the sectional plane (3); and, the axis of second light tunnel bore (810) has been raised 30* from the sample chamber axis (120), but is positioned to intercept light from point of intersection (700); the positioning of the second light tunnel bore (800) at an angle minimizes reflection of stray light from the walls of sample chamber (110) or the sample vessel (200) to the second photodetector (600); and, the axis of second light tunnel bore (810) has been shifted downward by approximately 2 mm to account for the index of refraction of water; the amount of shift is specific to the angle (30°) and to the dimensions of the colorimeter (1) described herein relative to the preferred embodiment for the measurement of hexavalent chromium in water; and, the interior surfaces of the colorimeter sample chamber (110), but not of transparent sample vessel (200), should be non-reflective; the configuration of the first light tunnel bore (500) and second light tunnel bore (800) of the colorimeter (1) are the preferred embodiment representing a simple means to shield the second photodetector (800) from the light from the light source (300).

8. The apparatus of claim 7 further comprising:

the first light tunnel bore (500) and the second light tunnel bore (800) are bored 5 mm in diameter; the second light tunnel (800) is approximately 38 mm long; the first light tunnel bore (500) from the first side (140) to the point of intersection (700) and from the second side (150) to the point of intersection (700) are each approximately 33 mm long; the sample chamber (110) is approximately 28 mm in diameter, and the outer and inner diameters of the sample vessel are approximately 27 mm and 25 mm, respectively; and the incident beam of the light source (300) is in the range of 367 to 375 nm; the light source (300) is provided by a light-emitting diode; the first photodetector (400) and the second photodetector (800), used for measuring the intensity of both the transmitted and scattered light, are infrared phototransistors used as photoconductive sensors; and, stabilized voltage is provided by an adjustable voltage regulator, an operational amplifier is used with inputs used as voltage followers; and, a red LED (1100) is used to indicate that power is switched on.

* * * * *